(12) United States Patent
Peterson et al.

(10) Patent No.: US 8,942,808 B2
(45) Date of Patent: Jan. 27, 2015

(54) STIMULATION PARADIGM TO IMPROVE BLOOD PRESSURE DIPPING IN AN IMPLANTABLE ELECTROACUPUNCTURE DEVICE

(71) Applicant: Valencia Technologies Corporation, Valencia, CA (US)

(72) Inventors: David K. L. Peterson, Valencia, CA (US); Stacy O. Greiner, Valencia, CA (US)

(73) Assignee: Valencia Technologies Corporation, Valencia, CA (US)

( * ) Notice: Subject to any disclaimer, the term of this patent is extended or adjusted under 35 U.S.C. 154(b) by 0 days.

(21) Appl. No.: 13/786,447

(22) Filed: Mar. 5, 2013

(65) Prior Publication Data

US 2014/0214116 A1 Jul. 31, 2014

Related U.S. Application Data

(60) Provisional application No. 61/609,875, filed on Mar. 12, 2012, provisional application No. 61/672,257, filed on Jul. 16, 2012, provisional application No. 61/676,275, filed on Jul. 26, 2012, provisional application No. 61/676,542, filed on Jul. 27, 2012.

(51) Int. Cl.
*A61N 1/00* (2006.01)
*A61B 17/00* (2006.01)
*A61N 1/36* (2006.01)

(52) U.S. Cl.
CPC .......... *A61N 1/36117* (2013.01); *A61N 1/3605* (2013.01); *A61N 1/36135* (2013.01)
USPC .............................. 607/44; 607/114; 606/204

(58) Field of Classification Search
USPC ...................................... 607/44, 116; 606/204
See application file for complete search history.

(56) References Cited

U.S. PATENT DOCUMENTS

| 4,031,899 A | 6/1977 | Renirie |
| 4,157,720 A | 6/1979 | Greatbatch |
| 4,345,604 A | 8/1982 | Renirie |

(Continued)

OTHER PUBLICATIONS

Dolan, "Superiority of Ambulatory Over Clinic Blood Pressure Measurement in Predicting Mortality—The Dublin Outcome Study," Hypertension 2005, 46: 156-161: originally published online Jun. 6, 2005.

(Continued)

*Primary Examiner* — Nicole F Lavert
(74) *Attorney, Agent, or Firm* — Bryant R. Gold

(57) ABSTRACT

A coin-sized implantable electroacupuncture (EA) device defines a stimulation paradigm, or stimulation regimen, that controls when EA stimulation pulses are applied to a selected acupoint, or other specified tissue location, to treat hypertension or nondipping. The stimulation regimen is applied when the patient is sleeping in order to minimize or mitigate the occurrence of nondipping or reverse dipping of the patient's blood pressure. In one embodiment, medical personnel, set a timing reference marker at the time of implant that defines how much time should elapse before a nighttime stimulation window opens that allows an EA stimulation session to be applied to the patient. In another embodiment, the patient sets the time when the nighttime stimulation window opens or when the EA stimulation session begins. Typically, an EA stimulation session is applied to the patient at a low duty cycle, e.g., only once a week during the nighttime.

7 Claims, 15 Drawing Sheets

(56) References Cited

U.S. PATENT DOCUMENTS

| | | | |
|---|---|---|---|
| 4,528,072 A | 7/1985 | Kurosawa | |
| 4,535,784 A | 8/1985 | Rohlicek | |
| 4,566,064 A | 1/1986 | Whitaker | |
| 5,195,517 A | 3/1993 | Chen | |
| 5,199,428 A | 4/1993 | Obel | |
| 5,211,175 A | 5/1993 | Gleason | |
| 5,250,068 A | 10/1993 | Ideguchi | |
| 5,251,637 A | 10/1993 | Shalvi | |
| 5,372,605 A | 12/1994 | Adams | |
| 5,544,656 A | 8/1996 | Pitsillides | |
| 5,707,400 A | 1/1998 | Terry | |
| 5,891,181 A | 4/1999 | Zhu | |
| 6,006,134 A | 12/1999 | Hill | |
| 6,178,352 B1 | 1/2001 | Gruzdowich | |
| 6,393,324 B2 | 5/2002 | Gruzdowich | |
| 6,522,926 B1 | 2/2003 | Kieval | |
| 6,658,298 B2 | 12/2003 | Gruzdowich | |
| 6,735,475 B1 | 5/2004 | Whitehurst | |
| 6,839,596 B2 | 1/2005 | Nelson | |
| 6,950,707 B2 | 9/2005 | Whitehurst | |
| 6,978,174 B2 | 12/2005 | Gelfand | |
| 7,003,352 B1 | 2/2006 | Whitehurst | |
| 7,013,177 B1 | 3/2006 | Whitehurst | |
| 7,046,499 B1 | 5/2006 | Imani | |
| 7,136,701 B2 | 11/2006 | Greatbatch | |
| 7,155,279 B2 | 12/2006 | Whitehurst | |
| 7,162,303 B2 | 1/2007 | Levin | |
| 7,171,266 B2 | 1/2007 | Gruzdowich | |
| 7,203,548 B2 | 4/2007 | Whitehurst | |
| 7,292,890 B2 | 11/2007 | Whitehurst | |
| 7,321,792 B1 | 1/2008 | Min et al. | |
| 7,373,204 B2 | 5/2008 | Gelfand | |
| 7,440,806 B1 | 10/2008 | Whitehurst | |
| 7,610,100 B2 | 10/2009 | Jaax | |
| 7,620,451 B2 | 11/2009 | Demarais | |
| 7,657,316 B2 | 2/2010 | Jaax | |
| 7,962,219 B2 | 6/2011 | Jaax | |
| 2003/0078642 A1 | 4/2003 | Malaney | |
| 2003/0158588 A1 | 8/2003 | Rizzo | |
| 2003/0187485 A1 | 10/2003 | Sturman | |
| 2003/0195583 A1 | 10/2003 | Gruzdowich | |
| 2005/0107832 A1 | 5/2005 | Bernabei | |
| 2005/0228460 A1 | 10/2005 | Levin | |
| 2005/0234533 A1 | 10/2005 | Schulman | |
| 2006/0041283 A1* | 2/2006 | Gelfand et al. | 607/44 |
| 2007/0005119 A1 | 1/2007 | Crohn | |
| 2007/0219595 A1* | 9/2007 | He | 607/36 |
| 2007/0255319 A1 | 11/2007 | Greenberg | |
| 2007/0265680 A1 | 11/2007 | Liu | |
| 2009/0210026 A1 | 8/2009 | Solberg | |
| 2009/0292341 A1 | 11/2009 | Parramon | |
| 2010/0042137 A1* | 2/2010 | Oronsky et al. | 606/204 |
| 2010/0069992 A1 | 3/2010 | Aghassian | |
| 2010/0211132 A1 | 8/2010 | Nimmagadda | |
| 2010/0324624 A1 | 12/2010 | Chang | |
| 2010/0327887 A1 | 12/2010 | Denison | |
| 2011/0106220 A1 | 5/2011 | DeGiorgio | |
| 2011/0112603 A1 | 5/2011 | DeGiorgio | |
| 2011/0172739 A1 | 7/2011 | Mann | |
| 2011/0218589 A1 | 9/2011 | DeGiorgio | |
| 2011/0218590 A1 | 9/2011 | DeGiorgio | |
| 2012/0022612 A1 | 1/2012 | Littlewood | |
| 2012/0259390 A1 | 10/2012 | Canion | |
| 2013/0041396 A1 | 2/2013 | Ryotokuji | |
| 2014/0214111 A1 | 7/2014 | Greiner | |
| 2014/0214112 A1 | 7/2014 | Greiner | |
| 2014/0214113 A1 | 7/2014 | Greiner | |
| 2014/0214114 A1 | 7/2014 | Greiner | |
| 2014/0214115 A1 | 7/2014 | Greiner | |
| 2014/0214116 A1 | 7/2014 | Peterson | |
| 2014/0214117 A1 | 7/2014 | Greiner | |
| 2014/0214118 A1 | 7/2014 | Greiner | |
| 2014/0214119 A1 | 7/2014 | Greiner | |
| 2014/0214124 A1 | 7/2014 | Greiner | |
| 2014/0214125 A1 | 7/2014 | Greiner | |
| 2014/0214126 A1 | 7/2014 | Greiner | |
| 2014/0214127 A1 | 7/2014 | Greiner | |
| 2014/0214128 A1 | 7/2014 | Peterson | |
| 2014/0214133 A1 | 7/2014 | Thenuwara | |
| 2014/0214134 A1 | 7/2014 | Peterson | |
| 2014/0214144 A1 | 7/2014 | Peterson | |

OTHER PUBLICATIONS

Kario K, Pickering TG, Umeda Y, et al. "Morning surge in blood pressure as a predictor of silent and clinical cerebrovascular disease in elderly hypertensives: a prospective study," Circulation. 2003; 107(1): 1401-1406.

Burnier M, Coltamai L, Maillard M, Bochud M, "Renal sodium handling and nighttime blood pressure," Smin Nephrol. 2007: 27(5): 556-571.

Bankir L., Bochud M, Maillard M, Bovet P, Gabriel A, Burnier M, "Nighttime blood pressure and nocturnal dipping are associated with daytime urinary sodium excretion in African subject," Hypertension 2008, 51(4): 891-898.

Boggia, J, Li Y, Thijs L, et. al., "Prognostic accuracy of day versus night ambulatory blood pressure; a cohort study," Lancet. 2007; 370(9594): 1219-1229.

Who Standard Acupuncture Point Locations in the Western Pacific Region, World Health Organization (WHO), Western Pacific Region, 2008 (updated and reprinted 2009), ISBN 978 92 9061 248 7. The Table of Contents, Forward (v-vi), General Guidelines for Acupuncture Point Locations (1-21).

Petrson, U.S. Appl. No. 13/776,155, filed Feb. 25, 2013.
Peterson, U.S. Appl. No. 13/769, 699, filed Feb. 18, 2013.
Peterson, U.S. Appl. No. 61/609,875, filed Mar. 12, 2012.
Peterson, U.S. Appl. No. 61/672,257, filed Jul. 16, 2012.
Thenuwara, U.S. Appl. No. 61/676,275, filed Jul. 26, 2012.
Peterson, U.S. Appl. No. 61/676,542, filed Jul. 27, 2012.
Greiner, U.S. Appl. No. 13/598,582, filed 08129/2012.Aug. 29, 2012.
Greiner, U.S. Appl. No. 13/622,653, filed Sep. 19, 2012.
Song, Kiseok, "The Compact Electro-Acupuncture System for Multi-Modal Feedback Electro-Acupuncture Treatment," 34th Annual International Conference of the IEEE EMBS, San Diego, CA, USA, Aug. 28-Sep. 1, 2012.

* cited by examiner

STIMULATION PARADIGM TO IMPROVE BLOOD PRESSURE DIPPING IN AN IMPLANTABLE ELECTROACUPUNCTURE DEVICE

RELATED APPLICATIONS

The present application claims the benefit of the following previously-filed U.S. provisional patent applications: U.S. Provisional Patent Application No. 61/609,875, filed Mar. 12, 2012; U.S. Provisional Patent Application No. 61/672,257, filed Jul. 16, 2012; U.S. Provisional Patent Application No. 61/676,275, filed Jul. 26, 2012; and U.S. Provisional Patent Application No. 61/676,542, filed Jul. 27, 2012. The present application is also related to the technology and methods disclosed in the following co-pending non-provisional U.S. Patent Applications of Applicant: (1) Implantable Electroacupuncture System and Method for Reducing Hypertension, application Ser. No. 13/598,582, filed Aug. 29, 2013, published Jul. 31, 2014 as Publication No. US 2014/0214115 A1; (2) Implantable Electroacupuncture System and Method for Treating Cardiovascular Disease, application Ser. No. 13/622,653, filed Sep. 19, 2012, published Jul. 31, 2014 as Publication No. US 2014/0214124 A1; (3) Electrode Configuration for an Implantable Electroacupuncture Device, application Ser. No. 13/776,155, filed Feb. 25, 2013, published Jul. 31, 2014 as Publication No. US 2014/0214144 A1; and (4) Circuits and Methods for Using a High Impedance, Thin, Coin-cell filer Type Battery in an Implantable Electroacupuncture Device, application Ser. No. 13/769,699, filed Feb. 18, 2013, published Jul. 31, 2014 as Publication No. US 2014/0214128 A1. All of the above-identified patent applications are incorporated herein by reference.

BACKGROUND

The present disclosure describes improvements to the manner of using and operating a small coin-sized electroacupuncture (EA) stimulator of the type described in the related patent applications referenced above, or equivalent small self-contained stimulators, adapted for implantation at selected tissue, nerve or acupoint target locations. More particularly, the present disclosure relates to a method of formulating or providing a stimulation paradigm for use within an implantable EA device that improves blood pressure (BP) "dipping" of a patient who uses the EA device for the treatment of hypertension or of a nondipping or reverse dipping condition.

Blood pressure "dipping" refers to changes that occur in a patient's blood pressure during the nighttime. Blood pressure, or "BP", in healthy individuals typically falls by about 15% during the nighttime or during sleep. Where blood pressure falls by less than 10% during the night, it is called nondipping, or reverse dipping if it rises. The term "nondipping" commonly includes reverse dipping.

Independent of the degree of hypertension, nondipping and reverse dipping have been identified as a strong risk factor for cardiovascular target organ damage. In an Irish study of over 5000 untreated hypertensive patients, the relative hazard ratio for each 10 mm Hg increase in systolic blood pressure (SBP) was 1.12 (1.06-2.28) for daytime and 1.21 (1.15-1.27) for nighttime blood pressure. See, e.g., Dolan, "Superiority of Ambulatory Over Clinic Blood Pressure Measurement in Predicting Mortality—The Dublin Outcome Study," *Hypertension* 2005, 46:156-161: originally published online Jun. 6, 2005.

Relatedly, a significant increase in blood pressure in the morning hours appears to be associated with worse cardiovascular outcomes. See, Kario K, Pickering TG, Umeda Y, et al. "Morning surge in blood pressure as a predictor of silent and clinical cerebrovascular disease in elderly hypertensives: a prospective study." *Circulation.* 2003; 107(1):1401-1406.

Nondipping or reverse dipping occurs in about 1 in 3 hypertensive people. See, e.g., Burnier M, Coltamai L, Maillard M, Bochud M, "Renal sodium handling and nighttime blood pressure," *Semin Nephrol.* 2007: 27(5):565-571; Bankir L, Bochud M, Maillard M, Bovet P, Gabriel A, Burnier M, "Nighttime blood pressure and nocturnal dipping are associated with daytime urinary sodium excretion in African subject," *Hypertension* 2008, 51(4):891-898.

In a large cohort of 7,458 patients from Europe, Asia, and South America, nighttime blood pressure, adjusted for daytime pressure was found to predict total cardiovascular, and noncardiovascular mortality, but daytime blood pressure, adjusted for nighttime blood pressure, only predicted noncardiovascular mortality. Thus, nighttime blood pressure is an important predictor of cardiovascular and other mortality— even more important than daytime blood pressure. See, Boggia, J, Li Y, Thijs L, et al., "Prognostic accuracy of day versus night ambulatory blood pressure: a cohort study," *Lancet.* 2007; 370 (9594): 1219-1229.

Recently, chronotherapeutics have arisen as a way to improve outcomes in consideration of the danger of nondipping or reverse dipping. Chronotherapeutics means the purposeful timing of medications to reduce both nondipping and quick morning rises in blood pressure. Antihypertensives are prescribed at nighttime for this improvement. Research by a group led by Hermida in Spain has shown that bedtime, as opposed to morning, dosing of various classes of antihypertensive medications leads to improvements in some key blood pressure parameters. Bedtime administration of telmisartan, for example, was shown to better reduce the mean nocturnal blood pressure than morning administration of the drug. Furthermore, telmisartan at night significantly reduced nondipping from 34% to 8% of patients as opposed to the failure to reduce nondipping when administered at morning. Results have been similar in the nighttime administration of ARBs, ACEi, CCBs, and alpha-blockers.

The present application does not deal with the administration of drugs to control hypertension. Rather, the application deals with applying electroacupuncture (EA) stimulation pulses to specific tissue locations for the purpose of treating hypertension, or other physiological maladies. But, as is discussed hereinafter, there is a need to know when such EA stimulation pulses should be applied to the specific tissue locations. The present application addresses that and other needs.

In accordance with the teachings of the applications referenced above, a self-contained, coin-sized stimulator may be implanted in a patient at or near a specified acupoint(s) in order to favorably treat a condition or disease of a patient. The coin-sized stimulator advantageously applies electrical stimulation pulses at very low levels and duty cycles in accordance with specified stimulation regimens through electrodes that form an integral part of the housing of the stimulator. A small battery inside of the coin-sized stimulator provides sufficient energy for the stimulator to carry out its specified stimulation regimen over a period of several months or years. Thus, the coin-sized stimulator, once implanted, provides an unobtrusive, needleless, long-lasting, elegant and effective mechanism for treating certain conditions and diseases that have long been treated by acupuncture or electroacupuncture.

It is noted that electroacupuncture, or EA, has long been used by certain acupuncturists as an alternative to classical acupuncture. In classical acupuncture treatment, needles are inserted into the patient's body at specified acupoints located throughout the human body. The location of the acupoints on the human body is well documented, see, e.g., *WHO STANDARD ACUPUNCTURE POINT LOCATIONS IN THE WESTERN PACIFIC REGION*, published by the World Health Organization (WHO), Western Pacific Region, 2008 (updated and reprinted 2009), ISBN 978 92 9061 248 7 (hereafter "*WHO Standard Acupuncture Point Locations* 2008"). The reference book, "*WHO Standard Acupuncture Point Locations* 2008" is incorporated herein by reference. It is significant that the location of the acupoints shown, e.g., in WHO Standard Acupuncture Point Locations 2008, has been determined based on over 2500 years of practical experience.

Despite the well-documented location of acupoints, it is noted that references to these acupoints in the literature have not always been consistent with respect to the format of the letter/number/name combination used to identify a particular acupoint. For example, some acupoints are identified by a name only, e.g., Tongi. The same acupoint may be identified by others by the name followed with a letter/number combination placed in parenthesis, e.g., Tongi (HT5). Other citations place the letter/number combination first, followed by the name, e.g., HT5 (Tongi). The first letter typically refers to a body organ, or other tissue location associated with, or affected by, that acupoint. However, usually only the letter is used in referring to the acupoint, but not always.

For purposes of this patent application, unless specifically stated otherwise, all references to acupoints that use the same name, or the same first letter and the same number, and regardless of slight differences in second letters and formatting, are intended to refer to the same acupoint. Thus, for example, the acupoint Neiguan is the same acupoint as Neiguan (P6), which is the same acupoint as Neiguan (PC6), which is the same acupoint as Neiguan (PC-6), which is the same acupoint as Neiguan (Pe-6), which is the same acupoint as P6, or PC6, or PC-6 or Pe 6.

In classical acupuncture treatment, once needles are inserted at a desired acupoint location(s), the needles are then mechanically modulated for a short treatment time, e.g., 30 minutes or less. The needles are then removed until the patient's next visit to the acupuncturist, e.g., in 1-4 weeks or longer, when the process is repeated. Over several visits, the patient's condition or disease is effectively treated, offering the patient needed relief and improved health.

In electroacupuncture treatment as described and practiced in the prior art, needles are inserted at specified acupoints, as in classical acupuncture treatment, but the needles, once inserted, are then connected to a source of electrical radio frequency (RF) energy, and electrical stimulation signals, at a specified frequency and intensity level, are then applied to acupoint(s), thereby also providing the patient with a measure of needed and desired treatment for his or her condition or disease.

One important use of the implantable EA devices described in the patent applications referenced above is for the treatment of hypertension. However, in order to maximize the efficacy of treating hypertension using an implantable EA device, there is a need for a preferred technique for configuring the stimulation paradigm provided by the EA device. Included in such stimulation paradigm, or stimulation regimen, is a preferred timing (time of day) for when such EA stimulation pulses should be applied to the specified tissue location. The present application addresses that need.

SUMMARY

Described herein are an implantable electroacupuncture (EA) device, and a method of using such device, that defines a stimulation paradigm, or stimulation regimen, that prescribes when EA stimulation pulses should be applied to a selected acupoint, or other specified tissue location known to affect a patient's blood pressure, in order to better treat hypertension. More particularly, as described herein, the stimulation regimen is applied during the nighttime, when the patient is typically sleeping, in order to minimize or mitigate the occurrence of nondipping or reverse dipping.

While numerous techniques may be used to apply EA stimulation pulses to specific tissue locations, e.g., acupoints, at a specified time of day (e.g., nighttime), one preferred technique relies on the patient, or a person assisting the patient (such as a spouse or nurse), to enable the implanted device at the desired start time, e.g., during the night time, using a simple turn-on technique, such as placing a magnet over the area with the EA stimulation device implanted in a prescribed sequence, in order to activate a magnetic reed switch contained within the device. Thereafter, the same start time will repeat every 7 days, (or 5 days, or some other time increment that is exactly n increments later, e.g., 3n or 8n, where n is 24 hours), unless the start time is reset by the patient.

Another preferred technique relies on the physician who implants the EA device to set a timing reference marker at the time of implant that defines how much time should elapse before a nighttime stimulation window opens that allows an EA stimulation session to be applied to the patient. The physician, or other medical personnel, may also set when within the stimulation window the EA stimulation session should commence. A "stimulation session," as used herein, is a prescribed time period, e.g., 30 minutes, during which time period the EA stimulation pulses are applied by the EA device to the patient. A "stimulation window," as used herein, is also a prescribed time period, e.g., 4-6 hours, during which time a stimulation session may commence.

In one preferred implementation of the invention, the stimulation session is applied to the patient during a time period that is most likely to be shortly after the patient has first fallen asleep, e.g., near or at the beginning of the stimulation window.

In another preferred implementation of the invention, the stimulation session is applied to the patient during a time period that is near the time when the patient will likely awake from his or her slumber, e.g., near or at the end of the stimulation window.

BRIEF DESCRIPTION OF THE DRAWINGS

The above and other aspects, features and advantages of the present invention will be more apparent from the following more particular description thereof, presented in conjunction with the accompanying drawings and appendix. These drawings illustrate various embodiments of the principles described herein and are a part of the specification. The illustrated embodiments are merely examples and do not limit the scope of the disclosure.

Appendix A contains selected material from Applicant's co-pending Patent Application, application Ser. No. 13/769, 699, filed Feb. 18, 2013, Publication No. US 2014/0214128, referenced above, supplemented with an additional schematic diagram of an IEAD, and a specification data sheet for a Real Time Clock Module.

Throughout the drawings, identical reference numbers designate similar, but not necessarily identical, elements.

DETAILED DESCRIPTION

Disclosed and claimed herein is a small electroacupuncture (EA) device, having one or more electrode contacts within or on its housing or closely coupled to its housing. The EA device is adapted to be implanted through a very small incision, e.g., less than 2-4 cm in length, directly adjacent to a selected acupuncture site (or target nerve/tissue location) known to moderate or affect a patient's physiological or health condition that needs treatment. (An acupuncture site, may also be referred to herein as an "acupoint.") Electroacupuncture stimulation pulses are applied by the EA device at the selected acupuncture site at a very low level and low duty cycle in accordance with a specified EA stimulation regimen. This stimulation regimen is designed to provide effective electroacupuncture treatment for the physiological or health condition(s) of the patient.

More particularly, in accordance with a preferred application of the teachings presented herein, the small EA device is implanted at or near a selected acupoint(s) of the patient, thereby allowing the EA stimulation pulses generated by the device to be applied at the selected acupoints of the patient in accordance with a specified stimulation regimen that is fashioned to treat hypertension. The stimulation regimen defines the type of stimulation pulses that are generated within an EA stimulation session, including the timing of when the stimulation session should commence. The EA stimulation session, which session typically has a duration of around 30 minutes, is preferably applied to the patient during the nighttime.

During the EA stimulation session, a continuous stream of stimulation pulses is generated having a very low duty cycle, e.g., pulses having a width of 2-20 milliseconds that occur once every 500 milliseconds (i.e., at a 2 Hz rate). Thus the duty cycle of the pulses being generated during a stimulation session is only, e.g., about 10 msec/500 msec=0.02, or 2%. In addition, the stimulation session is applied only about once a week, making the overall duty cycle much lower. Further, as mentioned, the EA stimulation session is applied at a selected time period when the patient is most likely to be asleep. Applying the EA stimulation session when the patient is asleep, for most patients, better moderates or controls any blood pressure nondipping or reverse dipping that might otherwise occur.

Figure 1:
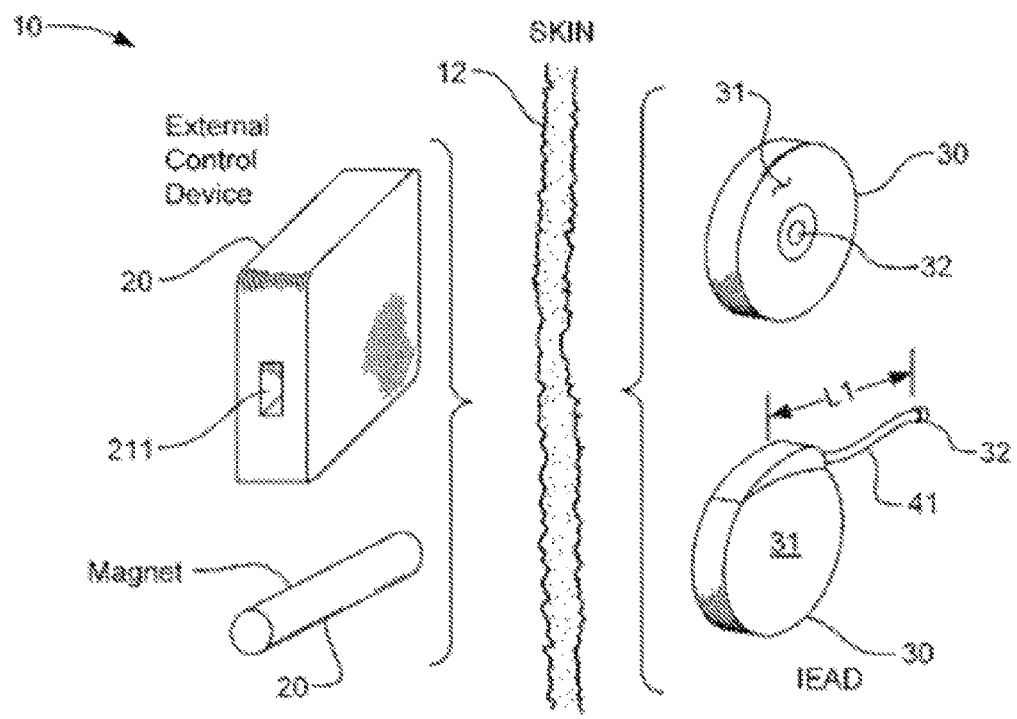
FIG. 1 is a block diagram that illustrates the two main components of a typical Electroacupuncture (EA) Stimulation System made as taught in the patent applications referenced above. Use of such EA Stimulation System (also referred to herein as an "EA System") includes: (1) an External Control Device (ECD); and (2) an Implantable Stimulator (also referred to herein as a "Implantable Electroacupuncture Device" or IEAD). Two variations of the IEAD are depicted, either one of which could be used as part of the EA System, one having electrodes formed as an integral part of the IEAD housing, and another having the electrodes at or near the distal end of a very short lead that is attached to the IEAD.

Turning first to FIG. 1, there is shown a perspective view of an exemplary EA System. The EA System has applicability to treating a variety of conditions, illnesses, disorders and deficiencies of a patient, and the present invention has applicability to all such applications.

As seen in FIG. 1, the EA System 10 includes two main components: (1) an External Control Device (ECD) 20 and (2) an Implantable ElectroAcupuncture Device 30, or IEAD 30. Two versions of the ECD 20 are included in FIG. 1. A first is a handheld electronic device that includes a port 211 enabling it to be coupled to a computer, or similar processor. A second is a magnet, typically a cylindrical magnet.

Two versions of an IEAD are also included in FIG. 18, either one of which may be used. One embodiment (top right of FIG. 1) has an electrode 32 that forms an integral part of the case 31 of the IEAD 30; and the other embodiment (lower right of FIG. 1) has an electrode 32 that is located at the end of a short lead 41 attached to the IEAD 30.

The IEAD 30, in one embodiment, is disc shaped, having a diameter of about 2 to 3 cm, and a thickness of about 2 to 4 mm. It is implanted just under the skin 12 of a patient near a desired acupuncture site. The desired acupuncture site is also referred to herein as a desired or target "acupoint." For reducing hypertension, the target acupoints of interest include acupoints PC5, PC6, LI4, ST36, ST37, LI11, LR3, and GB34.

The IEAD 30 includes an electrode 32 which may take various forms. A preferred electrode form is a smooth surface electrode, without any sharp or pointed edges.

For the embodiment shown in the top right portion of FIG. 1, and for the IEAD 30, the electrode 32 forms an integral part of the housing 31 of the IEAD 30, and is located on a "front" side of the IEAD housing approximately in the center of the housing. As used here, "front" means the side of the housing that fronts or faces the tissue to be stimulated. Frequently, but not always, the front side is the side of the IEAD housing 31 farthest from the skin layer 12, or deepest in the body tissue. Other embodiments may incorporate an electrode that is not centered in the housing 31, and that is not even on the front side of the housing, but is rather on an edge of the housing 31.

Alternatively, as shown in the bottom right of FIG. 1, the electrode 32 may be located at the distal end of a short lead 41, e.g., nominally 10-20 mm long, but in some instances it may be up to 50 mm long, implanted with a strain relief loop to isolate movement of the case from the electrode. The proximal end of the lead, which may also be referred to herein as a "pigtail lead", is attached to the IEAD 30 along an edge of the IEAD housing 31 or at a suitable connection point located on a side of the IEAD 30.

When implanted, the IEAD 30 is positioned such that the electrode 32 resides near, directly over, or otherwise faces the target tissue location, e.g., the desired acupoint or nerve that is to be stimulated. For those embodiments where the electrode 32 forms an integral part of the housing 31 of the IEAD 30, there is thus no need for a long lead that must be tunneled through body tissue or blood vessels in order to place the electrode at the desired acupoint or nerve. Moreover, even for those embodiments where a very short lead may be employed between the IEAD 30 and the electrode 32, the tunneling required, if any, is less than the present state of the art. In fact, with an electrode lead of between 20 mm and 50 mm in length, it is probable that no tunneling will be required. Further, because the electrode either forms an integral part of the IEAD housing 31, or is attached to the IEAD housing a very short pigtail lead, the entire IEAD housing 31 serves as an anchor to hold or secure the electrode 32 in its desired location.

For the embodiment depicted in the top right of FIG. 1 and as mentioned above, the electrode 32 is located in the center of the front side of the IEAD 30. As explained in more detail below, this positioning of the electrode 32 is only exemplary, as various types of electrodes may be employed, as well as various numbers of electrodes and relative positioning.

Still referring to FIG. 1, the EA System 10 also includes an external control unit, or ECD, 20. A USB port 211, located on one side of the ECD, allows it to be connected to a PC or notebook computer or other suitable processor for diagnostic, testing, or programming purposes. Other ports or connectors may also be used on the ECD 20, as needed. In its simplest form, however, the ECD 20 may take the form of a handheld magnet.

Figure 2A:
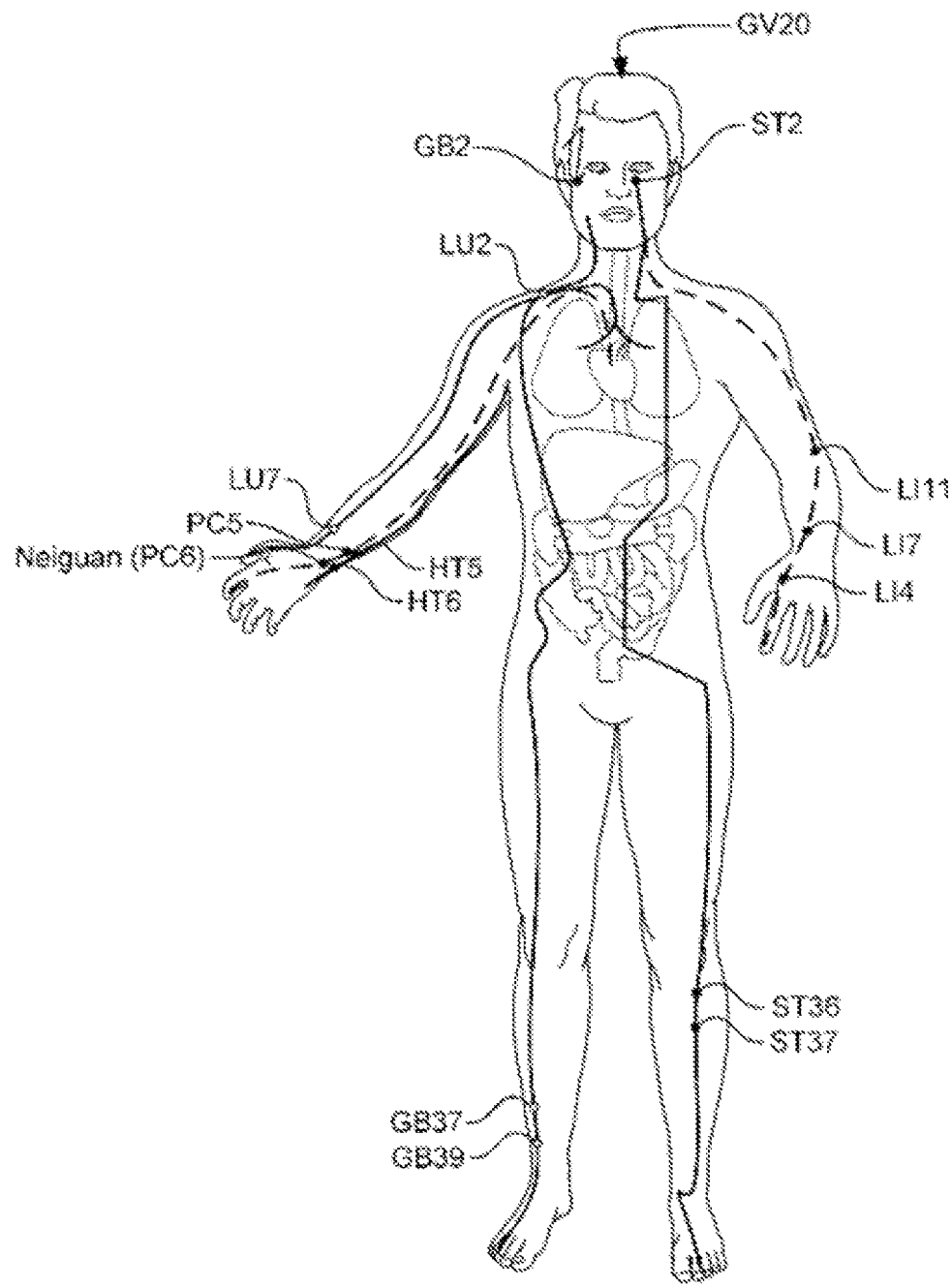
FIG. 2A is an illustration of the human body, and shows the location of some acupoints that may be used in providing electroacupuncture treatment for a particular condition or disease of a patient.

FIG. 2A shows an illustration of the human body, and shows the location of some of the acupoints used in electroacupuncture for the treatment of hypertension. For reducing hypertension, the target acupoints of interest include acupoints PC5, PC6, LI4, ST36, ST37, LI11, LR3, and GB34.

Figure 2B:
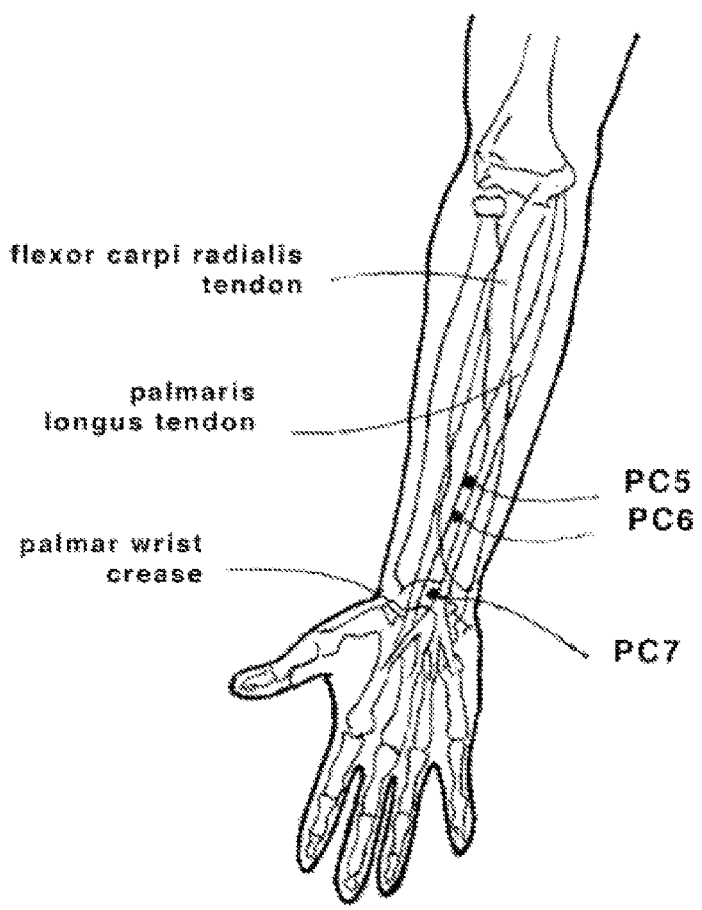
FIG. 2B is an illustration of the human hand, showing with more particularity the location of acupoints PC5 and PC6.

FIG. 2B is an illustration of the human hand, showing with more particularity the location of acupoints PC5 and PC6. The acupoint PC5 is on the anterior aspect of the forearm, between the tendons of the palmaris longus and the flexor carpi radialis, about 3 B-cun proximal to the palmar wrist crease. The measurement system using units of "B-cun" is a proportional bone (skeletal) measurement system described in the *WHO Standard Acupuncture Point Locations* 2008 reference book cited previously. See, in particular, pages 2, 11-13 and 20-21 of that reference book, especially FIG. 20, on page 20, and FIG. 21, on page 21. However, for an average-sized adult, a measurement of 1.5 B-cun may be considered to be approximately 1.5 inches. Further details regarding the description and location of acupoints PC5 and PC6 may also be found in the "WHO Standard Acupuncture Point Locations 2008" reference book, previously referenced.

Figure 2C:
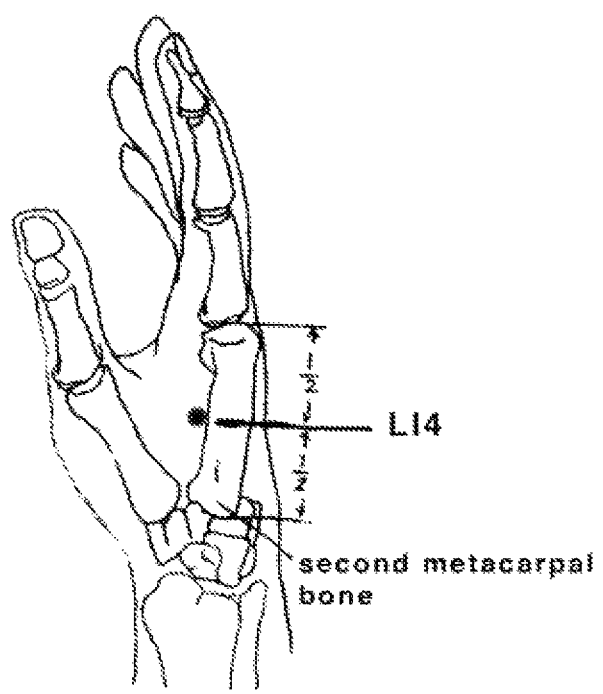
FIG. 2C is another illustration of the human hand, showing the location of acupoint L14.

FIG. 2C is another illustration of the human hand, showing the location of acupoint LI4. The acupoint LI4 is on the dorsum of the hand, radial to the midpoint of the second metacarpal bone.

Figure 2D:
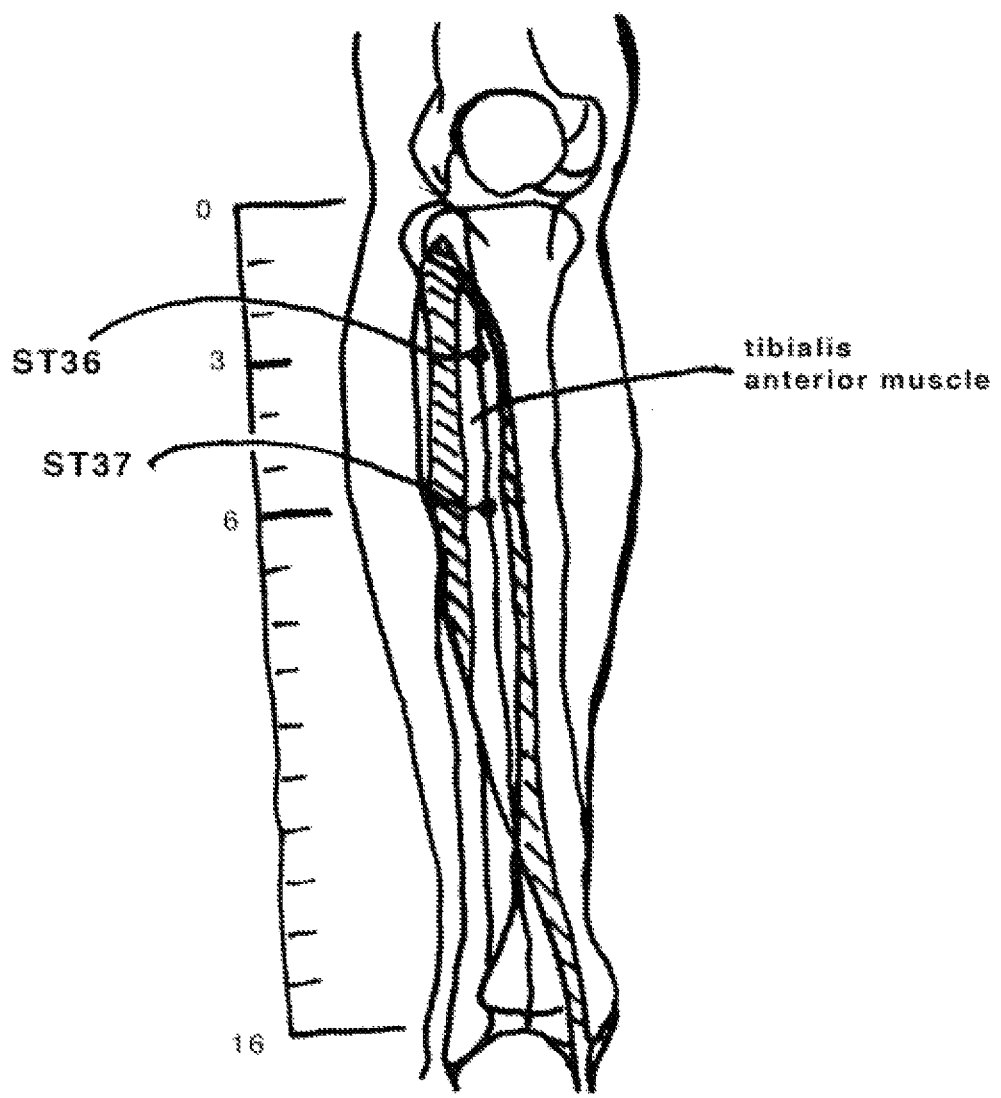
FIG. 2D is an illustration of a human leg, illustrating the location of acupoints ST36 and ST37.

FIG. 2D is an illustration of a human leg, illustrating the location of acupoints ST36 and ST37. As seen in FIG. 2D, the acupoint ST36 is on the anterior aspect of the leg, on the line connecting ST35 with ST41, 3 B-cun inferior to ST35. It should be noted that ST36 is located on the tibialis anterior muscle. The acupoint ST37 is also located on the anterior aspect of the leg, on the line connecting ST35 with ST41, 6 B-cun interior to ST35. ST37 is also located on the tibial is anterior muscle.

Figure 2E:
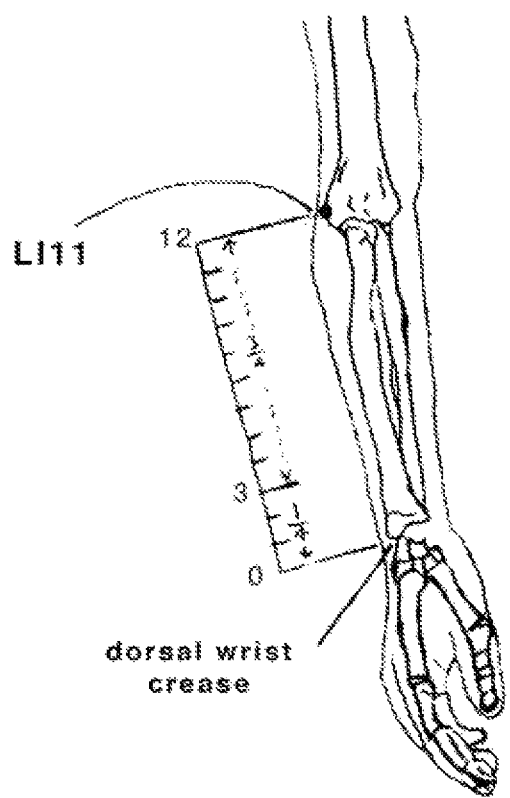
FIG. 2E is an illustration of the human hand, showing the location of acupoint LI11.

FIG. 2E is an illustration of the human forearm, showing the location of acupoint LI11. As seen in this figure, acupoint LI11 is on the lateral aspect of the elbow, at the midpoint of the line connecting LU5 with the lateral epicondyle of the humerus. When the elbow is fully flexed, LI11 is located in the depression on the lateral end of the cubital crease.

Figure 2F:
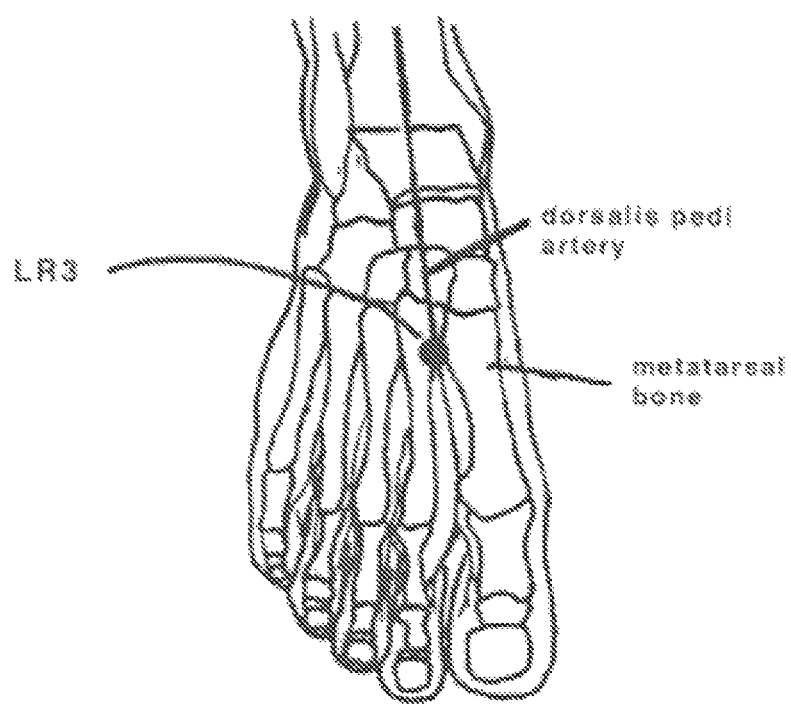
FIG. 2F is an illustration of the foot, showing the location of acupoint LR3.

FIG. 2F is an illustration of the foot, showing the location of acupoint LR3. As seen in this figure, acupoint LR3 is located on the dorsum of the foot, between the first and second metatarsal bones, in the depression distal to the junction of the bases of the two bones, over the dorsalis pedis artery. Acupoint LR3 can be felt in the depression when moving proximally from LR2 in the gap between the first and second metatarsal bones towards the base of two metatarsal bones.

Figure 2G:
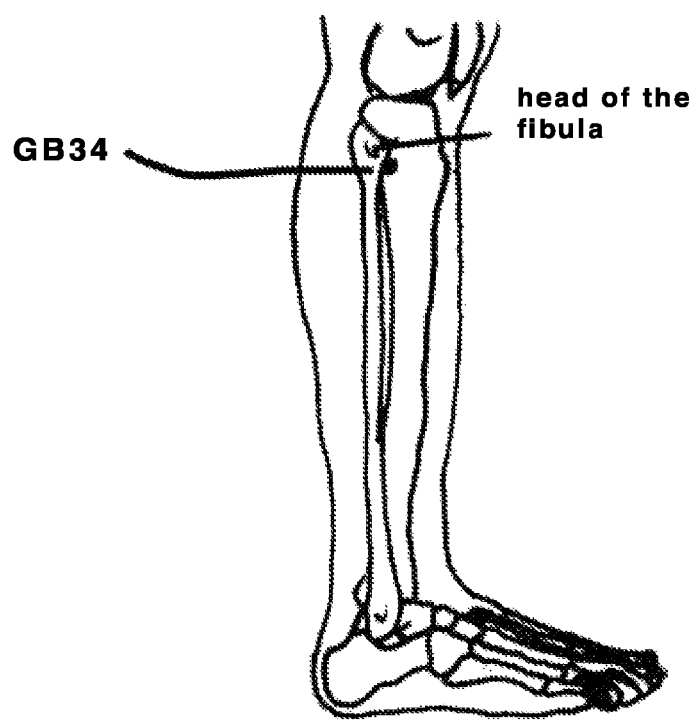
FIG. 2G is an illustration of the lower half of the leg, showing the location of acupoint GB34.

FIG. 2G illustrates the location of acupoint GB34 on the lower half of the leg, showing the location of acupoint GB34. As can be seen from this figure, GB34 is located on the fibular aspect of the leg, in the depression anterior and distal to the head of the fibula.

Figure 3:
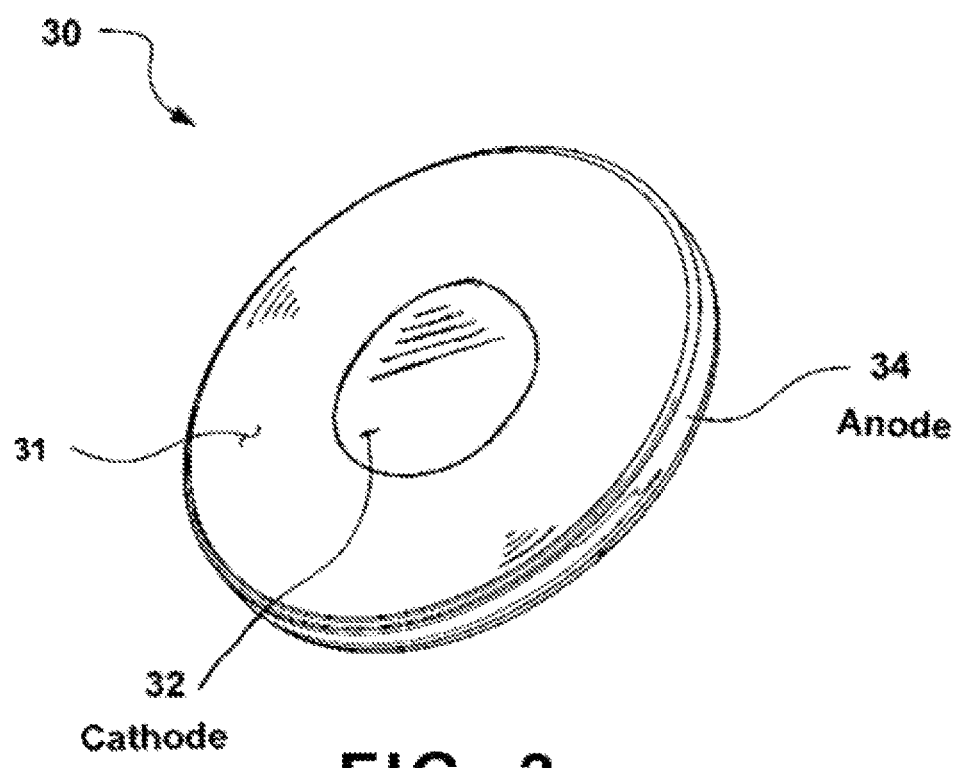
FIG. 3 shows one embodiment of a coin-sized Implantable ElectroAcupuncture Device (IEAD), and illustrates a representative electrode pair, both cathode and anode, placed on the housing of the IEAD.

Next, with reference to FIG. 3, there is shown an illustration of the preferred configuration for the IEAD 30 shown in the upper right portion of FIG. 1. As seen in FIG. 3, the IEAD 30 is disc shaped, having a diameter of about 2 to 3 cm, and a thickness of about 2 to 3 mm. It is implanted just under the Skin 12 of a patient at or near a desired acupoint. As previously indicated, for reducing hypertension, the target acupoints of interest include acupoints PC5, PC6, LI4, ST36, ST37, LI11, LR3, and GB34.

As seen in FIG. 3, the IEAD 30 includes at least two electrodes, an anode 34 and a cathode 32. One of these two electrodes may comprise the case of the IEAD 30. A preferred IEAD configuration uses a circular central cathode electrode 32 positioned in the center of one side of the case or housing 31 of the IEAD 30. An anode electrode, configured as a ring electrode 34, is positioned around the edge of the disc-shaped IEAD 30. The advantage of the electrode configuration shown in FIG. 3 is described in more detail in Applicant's co-pending U.S. Patent Application, Electrode Configuration for an Implantable Electroacupuncture Device, application Ser. No. 13/776,155, filed Feb. 25, 2013, Publication No. US 2014/0214144, previously incorporated herein by reference.

When implanted, the IEAD 30 is positioned such that the electrode 32 resides near, directly over, or on, the desired acupoint. Because the electrode forms an integral part of the IEAS housing 31, the entire IEAS housing 31 serves as an anchor to hold or secure the electrode 32 in its desired location.

Figure 4:
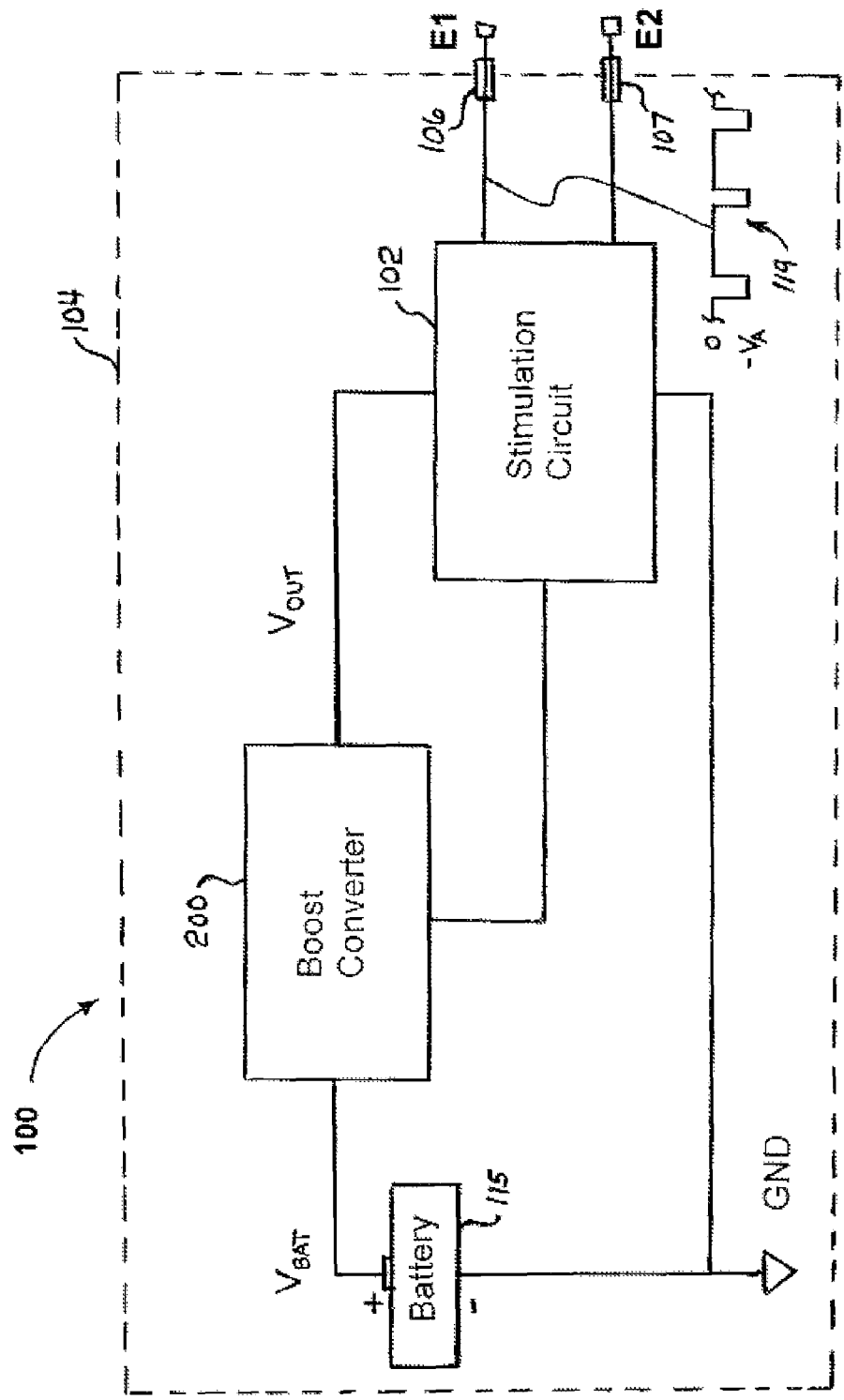
FIG. 4 is a functional block diagram that illustrates a representative configuration of an IEAD that uses an implantable battery, having a battery voltage $V_{BAT}$ that must be boosted to a different voltage $V_{OUT}$ by a boost converter circuit in order for a stimulation circuit within the IEAD to function efficiently.

FIG. 4 shows a functional block diagram that illustrates a representative electrical configuration of an EA device 100 that uses an implantable battery having a battery voltage $V_{BAT}$ that must be boosted to a different voltage $V_{OUT}$ by a boost converter circuit in order for a stimulation circuit within the IEAS device to function efficiently.

Thus, as seen in FIG. 4, a representative configuration of an implantable EA device 100 includes an implantable battery 115 providing a battery output voltage $V_{BAT}$. Also included within the EA device 100 is a Boost Converter circuit 200 and Stimulation Circuitry 102. The battery 115, Boost Converter circuit 200 and Stimulation Circuitry 102 are all housed within an hermetically sealed housing 104.

The Stimulation Circuitry 102 of the EA device 100 generates a sequence of stimulation pulses that are delivered to electrodes E1 and E2, through feedthrough terminals 106 and 107, respectively, in accordance with a prescribed stimulation regimen. For an EA device of the type disclosed in the patent applications previously referenced, the prescribed stimulation regimen may comprise a continuous stream of stimulation pulses having a fixed amplitude, e.g., $V_A$ volts, a fixed pulse width, e.g., 0.5 msec, and at a fixed frequency, e.g., 2 Hz, during each stimulation session. The stimulation session, also as part of the stimulation regimen, is generated at a low duty cycle, e.g., for 30 minutes once each week.

In one preferred embodiment, the electrodes E1 and E2 form an integral part of the housing 104. In other preferred embodiments, the electrodes E1 and/or E2 are carried on the surface of the housing 104, or coupled to a respective feedthrough terminal protruding from a surface of the housing 104, through a very short lead. In other embodiments, one of the electrodes, E1 or E2, may comprise the case of the housing 104, thereby eliminating the need for one of the feedthrough terminals.

Typically, the electrode E2 functions as an anode, or positive (+) electrode, and the electrode E1 functions as a cathode, or negative (−) electrode. This allows the current associated with the stimulation pulses to be sourced from the Stimulation Circuit 102 through one terminal, and sunk back to the Stimulation Circuit 102 through the other terminal. It is common when using implantable neural stimulators, such as the EA device 100, to utilize negative, or cathodic, pulse stimulation, as illustrated in the waveform diagram 119 shown in FIG. 4 in the lower right corner of the housing 104. In such stimulation, the electrical pulses comprise negative-going pulses, starting at a reference voltage of 0 volts, and having a pulse amplitude, e.g., of $-V_A$ volts, where the magnitude $V_A$ is close to the magnitude of $V_{OUT}$.

The battery 115 provides all of the operating power needed by the EA device 100. The battery voltage $V_{BAT}$ is not the optimum voltage needed by the circuits of the EA device, including the stimulation circuitry, in order to efficiently generate stimulation pulses of amplitude, e.g., $-V_A$ volts. The amplitude $V_A$ of the stimulation pulses is typically many times greater than the battery voltage $V_{BAT}$. This means that the battery voltage must be "boosted", or increased, in order for stimulation pulses of amplitude $V_A$ to be generated. Such "boosting" is done using the Boost Converter circuit 200. That is, it is the function of the Boost Converter circuit 200 to take its input voltage, $V_{BAT}$, and convert it to another voltage, e.g., $V_{OUT}$, which voltage $V_{OUT}$ is needed by the Stimulation Circuit 102 in order for the EA device 100 to perform its intended function.

One advantageous feature of the invention shown in FIG. 4 is that it can perform its stimulation function for a long period of time, typically about 3 years, using only the energy stored within a thin, inexpensive, coin-cell battery. It is able to do this through careful power management, as described more fully in Applicant's co-pending U.S. Patent Application, Circuits and Methods for Using a High Impedance, Thin, Coin-cell Type Battery in an Implantable Electroacupuncture Device, application Ser. No. 13/769,699, Filed Feb. 18, 2013, Publication No. US 2014/0214128, which application has been previously incorporated herein by reference.

As shown, e.g., in FIG. 14A of the application referenced in the preceding paragraph, the stimulation circuitry 102 (FIG. 4) may be realized using a micro-controller integrated circuit (IC) U2 which generates all of the operating control signals needed to guide other circuits, including the Boost Converter circuit 200, to generate the desired stream of stimulation pulses. These other circuits include a programmable current source IC U3, an analog switch U5, and a magnetic sensor U4. The micro-controller IC U2 in that configuration is driven by a clock circuit that includes a crystal oscillator to provide a very stable frequency reference. However, when the stimulus pulses are not being generated—which is most of the time given the very low duty cycle of operation, e.g., T3/T4 is less than 0.05—the micro-controller U2 is able to go into a very low power consuming sleep state, thereby conserving power.

In order for the present invention of provide accurate chronotherapeutics, it would be desirable to use a crystal time base. In the existing micro-controller U2 design, however, a crystal time base (operating all the time) would roughly double the battery current between therapy sessions, thereby taking the nominal longevity of the implantable electroacupuncture device (IEAD) down roughly from 3 years to 2 years. Reducing the longevity of the IEAD by a factor of ⅓ is not viewed as an acceptable tradeoff to provide accurate chronotherapeutics. Hence, what is needed is a design, or alternate approach, whereby an accurate time base could be provided without sacrificing a significant loss in longevity.

One way to accomplish this desired result is to add another small IC, e.g., U6, to the circuits of the IEAD that functions as a real time clock (RTC). Such RTC may be realized from a very small device (3.2×1.5 mm) that runs on 360 nanoAmps (nA) of current. Such device, referred to as a Real Time Clock Module is commercially available from Micro Crystal AG, of Grenchen, Switzerland, as part number RV-4162-C7. Use of such RTC Module would replace the crystal presently used with the micro-controller U2, and could wake up the micro-controller when needed, and put it in a shut-down (sleep) state when not needed, which shut down mode is even a lower power state than is achieved with the sleep state controlled by the present crystal oscillator.

Submitted herewith is Appendix A, which contains (i) FIG. 14A from Applicant's co-pending Patent Application referenced above (application Ser. No. 13/769,699, Filed Feb. 18, 2013, Publication No. US 2014/0214128); (ii) relevant pages from the Ser. No. 13/769,699 application that describe selected aspects of the operation of FIG. 14A; (iii) a data sheet that describes the RV-4162-C7 Real Time Clock Module, made by Micro Crystal AG; and (iv) a schematic drawing that illustrates one manner in which the RV-4162-C7 RTC Module could be coupled with the micro-controller circuit U2 and the overall schematic of the IEAD. Appendix A is incorporated herein by reference.

The housing 104 of the EA device 100, in one preferred embodiment, has a shape and size that is approximately the same as a U.S. quarter, or smaller. That is, the EA device 100 is disc-shaped, having a diameter of about 22 mm and a thickness of approximately 2 to 3 mm. Electrodes E1 and E2 are preferably mounted to, or form an integral part of, the housing 104. In one preferred embodiment, there is one cathodic electrode centrally located on the underneath side of the coin-shaped housing (where "underneath" in this context means that side of the housing farthest away from the skin). There is also one ring anodic electrode around the perimeter edge of the disc-shaped housing.

In another preferred embodiment, there are two cathodic electrodes, one on each side (over and under) of the coin-shaped housing, and one ring anodic electrode around the perimeter of the coin- or disk-shaped housing. In a variation of this embodiment, the cathodic and/or anodic electrodes are further segmented, or partitioned, so that only a portion of the electrode surface area may be selectively activated at any given time. These electrode configurations are further described in Applicant's co-pending U.S. patent application Ser. No. 13/776,155, filed Feb. 25, 2013, Publication No. US 2014/0214134, previously referenced.

Figure 5:
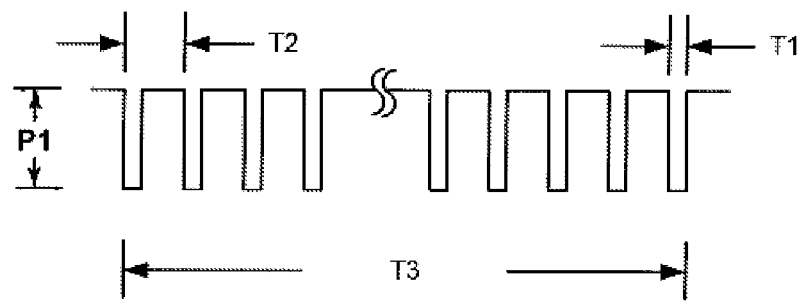
FIG. 5 is a timing diagram that illustrates a train of stimulation pulses applied during a stimulation session that has a duration of T3 minutes, which stimulation session is generated, as seen in FIG. 6, every T4 minutes. The individual stimulation pulses have a duration of T1 seconds and occur every T2 seconds. As explained more fully below, the time period T1 is much less than the time period T2, and the time period T2 is much less than the time period T3, and the time period T3 is much less than the time period T4. Thus, the stimulation pulses are applied at a very low duty cycle. Typically, the time units used to express the time period T1 are milliseconds, the time units used to express the time period T2 are seconds, the time units used to express the time period T3 are minutes or hours, and the time units used to express the time period T4 are days or weeks.

Next, with reference to FIG. 5, a timing diagram is shown that illustrates a train of stimulation pulses applied during a stimulation session. The stimulation session has a duration of T3 minutes, which stimulation session is generated every T4 minutes. The individual stimulation pulses have a duration of T1 seconds and occur every T2 seconds. As explained more fully below, the time period T1 is much less than the time period T2, and the time period T2 is much less than the time period T3, and the time period T3 is much less than the time period T4. Thus, the stimulation pulses are applied at a very low duty cycle. Typically, the time units used to express the time period T1 are milliseconds, the time units used to express the time period T2 are seconds, the time units used to express the time period T3 are minutes or hours, and the time units used to express the time period T4 are days or weeks.

It is noted that the stimulation pulses illustrated in FIG. 5 are negative stimulation pulses, as shown previously in lower right corner of FIG. 4. These pulses have an amplitude of P1 (measured in units of voltage or current), with each pulse comprising a negative-going pulse having a duration of T1. The time period T1 is often referred to as the "pulse width". One pulse occurs every T2 seconds. Thus the rate or frequency of the stimulation pulses is 1/T2 Hz. For example, if T1 is 0.2 milliseconds (200 microseconds) and T2 is 0.5 seconds (or 500 milliseconds), then a pulse train of stimulation pulses, each having a duration or width of 200 microseconds, is generated at a rate of 2 pulses per second, or 2 Hz. Other types of stimulation pulse waveforms may be used, as are known in the art. The shape of the stimulus pulses used during a stimulation session is not important for purposes of the present invention. All that needs to be understood is that the EA device produces a train of stimulus pulses during a stimulation session, wherein each stimulus pulse has a width of T1 seconds, and where the stimulus pulses occur every T2 seconds, and where the ratio of T1/T2 is small.

Figure 6:
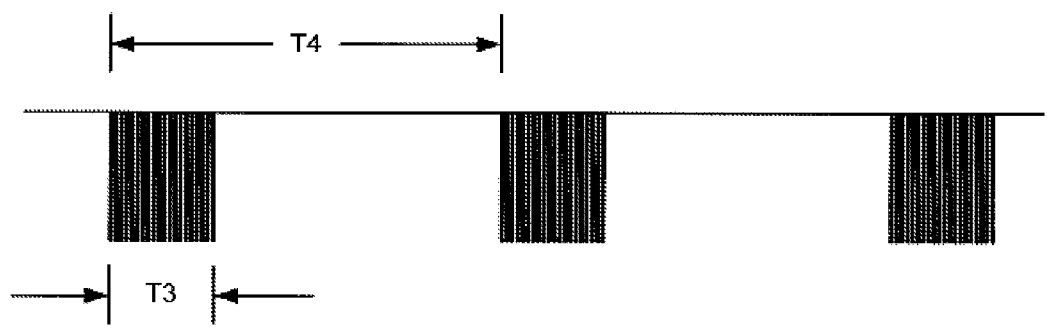
FIG. 6 is a timing diagram that illustrates, using a more compressed time scale than FIG. 5, the application of stimulation sessions having a duration of T3 minutes every T4 days.

FIG. 6 shows a timing diagram that illustrates, using a more compressed time scale than FIG. 5, the application of stimulation sessions having a duration of T3 minutes every T4 days. As has been indicated previously, a representative duration for a stimulation session is 30 minutes, and a representative frequency of the stimulation sessions is once a week (i.e., T4=7 days=168 hours=10,080 minutes).

As has been indicated above, it is a key purpose of the present invention to apply a stimulation session to a patient at a time when the patient is, or is likely to be, asleep. One straightforward way of accomplishing this task is to pre-program the EA device to generate a stimulation session that begins at the same time, e.g., 11:30 pm, every 7 days. The start time may be manually triggered or set by the patient, or by a person assisting the patient (such as a spouse or nurse), using a manually triggered start mechanism. One such mechanism would be to employ a magnetic reed switch with simple logic control within the EA device. For example, if the magnetic reed switch were to be closed by the presence of a magnetic field three times over a span of three seconds, then that would signal the device to begin the stimulation session. Such beginning would also reset the clock within the EA device so that it would, unless reset, start a stimulation session every 7 days after the commencement of the first session. The manual triggering mechanism used in such a situation could be a permanent magnet that the patient, or his or her assistant, moves over the implant site three times in the space of three seconds.

Besides the straightforward way of commencing the stimulation session during a time when the patient is likely to be asleep, described above, other more controlled ways may also be employed.

Figure 7:
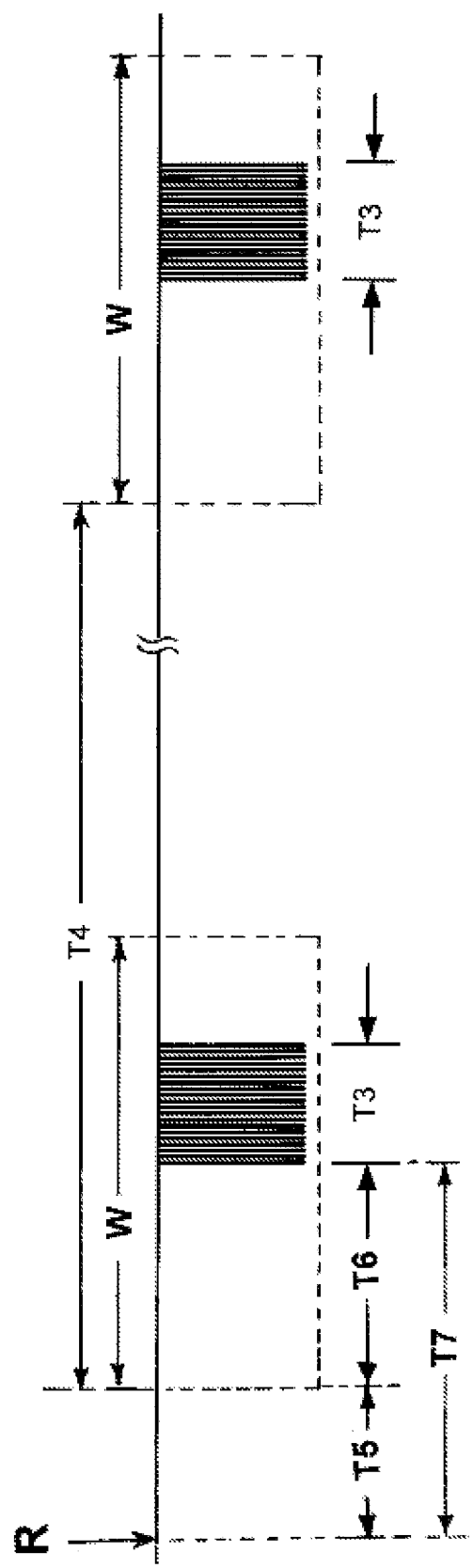
FIG. 7 is a timing diagram that illustrates one representative approach for applying a stimulation session having a duration of T3 minutes during a stimulation window having a duration of W hours, where the stimulation window opens (or is activated) a prescribed time period T5 after the occurrence of a reference marker R. The stimulation session begins within the stimulation window at a prescribed time period T6 after the stimulation window opens.

For example, FIG. 7 shows a timing diagram that illustrates one representative approach for applying a stimulation session having a duration of T3 minutes during a stimulation window having a duration of W hours, where the stimulation window opens (or is activated) a prescribed time period T5 after the occurrence of a reference marker R. The stimulation session begins within the stimulation window at a prescribed time period T6 after the stimulation window opens.

For example, when the doctor implants the EA device, using a programming module, e.g., the external controller 20, he or she sets a timing reference marker R at the time of implant that defines how much time should elapse before a nighttime stimulation window W opens that allows an EA stimulation session to be applied to the patient. The physician, or other medical personnel, may also set when within the stimulation window the EA stimulation session should commence. A "stimulation window," as used herein, is a prescribed time period, e.g., 4-6 hours, during which time a stimulation session may commence.

In one preferred implementation of the invention, the stimulation session is applied to the patient during a time period that is most likely to be shortly after the patient has first fallen asleep, e.g., near or at the beginning of the stimulation window.

In another preferred implementation of the invention, the stimulation session is applied to the patient during a time period that is near the time when the patient will likely awake from his or her slumber, e.g., near or at the ending of the stimulation window.

By way of example, if the physician wants the stimulation window to begin at 11 pm on the day following the implant procedure, and if s/he performs the implant procedure at 2:00 pm, s/he would set 2 pm as the reference time, and would then set the time T5 to be 33 hours, or 9 hours until 11 pm of the day of the implant plus 24 hours more to have the time the stimulation session begins as 11 pm on the day after the implant. The physician would also set the time T6 to a suitable value, e.g., 1 hour, which would cause the stimulation session to begin at midnight, 1 hour after the stimulation window opened.

Figure 8:
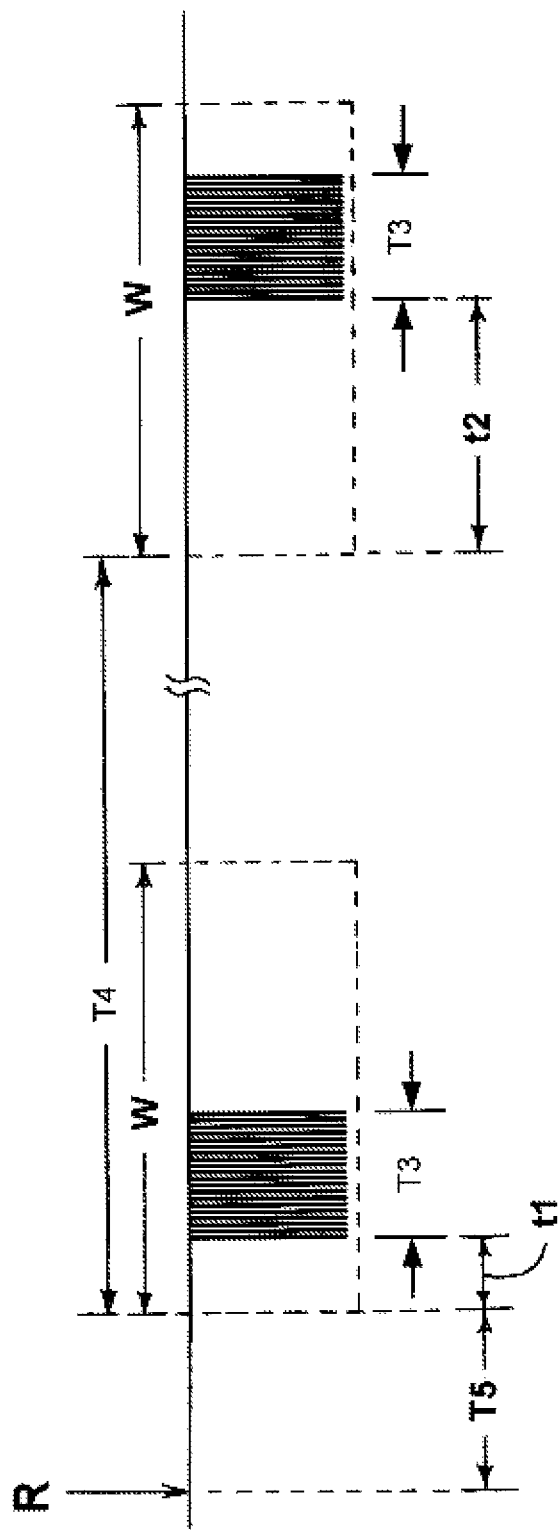
FIG. 8 is a timing diagram that illustrates another representative approach for applying a stimulation session having a duration of T3 minutes during a stimulation window having a duration of W hours, where the stimulation window opens (or is activated) a prescribed time period T5 after the occurrence of a reference marker R. The stimulation session begins within the stimulation window at a variable time t1 after the stimulation window opens. The variable time t1 may be determined by sensing a physiological parameter having a value indicative of a sleep state of the patient within whom the IEAS device is implanted.

FIG. 8 is a timing diagram that illustrates another representative approach for applying a stimulation session having a duration of T3 minutes during a stimulation window having a duration of W hours, where the stimulation window opens (or is activated) a prescribed time period T5 after the occurrence of a reference marker R. In accordance with the approach shown in FIG. 8, the stimulation session begins within the stimulation window at a variable time t1 after the stimulation window opens. The variable time t1 may be determined by sensing a physiological parameter having a value indicative of a sleep state of the patient within whom the IEAS device is implanted. For example, the patient may have an expandable chest cuff that monitors the breathing rate of the patient. When the breathing rate slows to a rate indicative of sleep, then a sensor coupled to the cuff would send a signal to the EA device that would trigger the beginning of the stimulation session.

Other sensors could of course be used, many of which would be less invasive than a chest cuff. For example, a simple temperature sensor could be included in the EA device to measure the temperature of the patient's tissue surrounding the EA device. When asleep, the body temperature typically drops a few tenths of a degree, and this change in body temperature could trigger the time to commence a stimulation session.

In a similar manner, an optical sensor employed within the EA device may be used to measure the optical properties of the blood flowing in an artery near the implant site. From these properties the saturated oxygen concentration, $SO_2$, within the blood can be roughly measured. When the $SO_2$ level drops a few percentage points, that usually indicates the patient is asleep, and this could be used to trigger the beginning of the stimulation session.

As described above, it is thus seen that the invention(s) provides a way to begin a stimulation session of EA stimulation pulses during a time when the patient is likely to be asleep. Applying EA stimulation when the patient is sleeping allows blood pressure nondipping, or reverse dipping, to be better controlled and managed.

Figure 9:
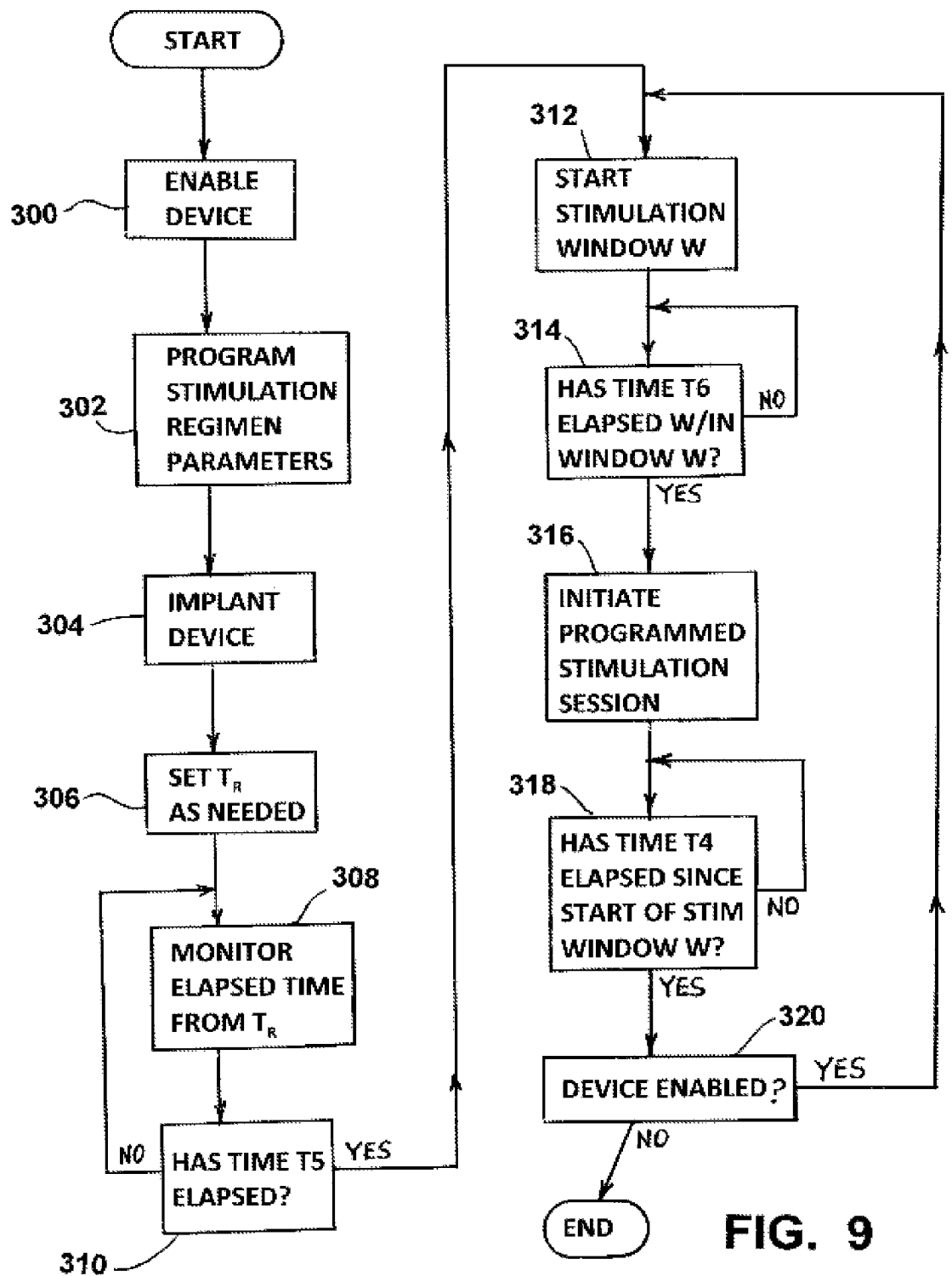
FIG. 9 is a flow diagram illustrating one representative approach for generating the sequence of stimulation windows and sessions depicted in the timing diagram of FIG. 7.

FIG. 9 shows a flow diagram illustrating one representative approach for generating the sequence of stimulation windows and stimulation sessions depicted in the timing diagram of FIG. 7.

As seen in FIG. 9, when the physician implants the EA device, the device must be enabled (block 300). Once enabled, using the external controller 20 or an equivalent programmer, the physician (or other medical personnel) programs the needed parameters into the EA device (block 302). These parameters include the time periods T5 and T6. For example, T5 is the number of hours after the reference time TR is set when a stimulation window is to be opened. If the implant operation is performed at 10 am, and the stimulation window is to be opened at 10 pm, then T5 would be set to 12 hours. The time T6 is the time after the stimulation window is opened that the actual stimulation session is to begin. For example, if the physician wants the stimulation session to begin a 11 pm, and the stimulation window is set to open at 10 pm, then T6 would be set to 1 hr.

Still referring to FIG. 9, after the needed parameters of the EA device have been programmed into the device, the device is implanted (block 304). If the reference marker R needs to be set, then it is set at this time (block 306). In some embodiments, R may be set with a magnet. Typically, however, R would be set at the same time, or close to the same time, that the other parameters are programmed (block 302) into the device.

The timing circuits of the EA device then monitor elapsed time that has occurred since the time $T_R$ (block 308). If this elapsed time has not yet reached the value of T5, then the monitoring of elapsed time continues (NO branch of block 310). Once this elapsed time is equal to T5 (YES branch on block 310), then the stimulation window begins (block 312).

Once the stimulation window has been opened, or started, the elapsed time is then monitored to determine if the elapsed time since the stimulation window commenced has reached the programmed time T6 (block 314). If it has, then a stimulation session begins (block 316). The stimulation session then continues for its programmed duration, time T3.

When the stimulation session ends, the elapsed time since the start of the stimulation window W continues to be monitored (block 318). When the elapsed time since the start of the last stimulation window reaches time T4 (YES branch of block 318), then a determination is made as to whether the EA device is still enabled (block 320). If it is (YES branch of block 320) then the process cycle begins again (at block 312) and the next stimulation window W is started. This process continues (blocks 312, 314, 316, 318 and 320) for as long as the EA device remains enabled, with a new stimulation window being opened every T4 days.

Figure 10:
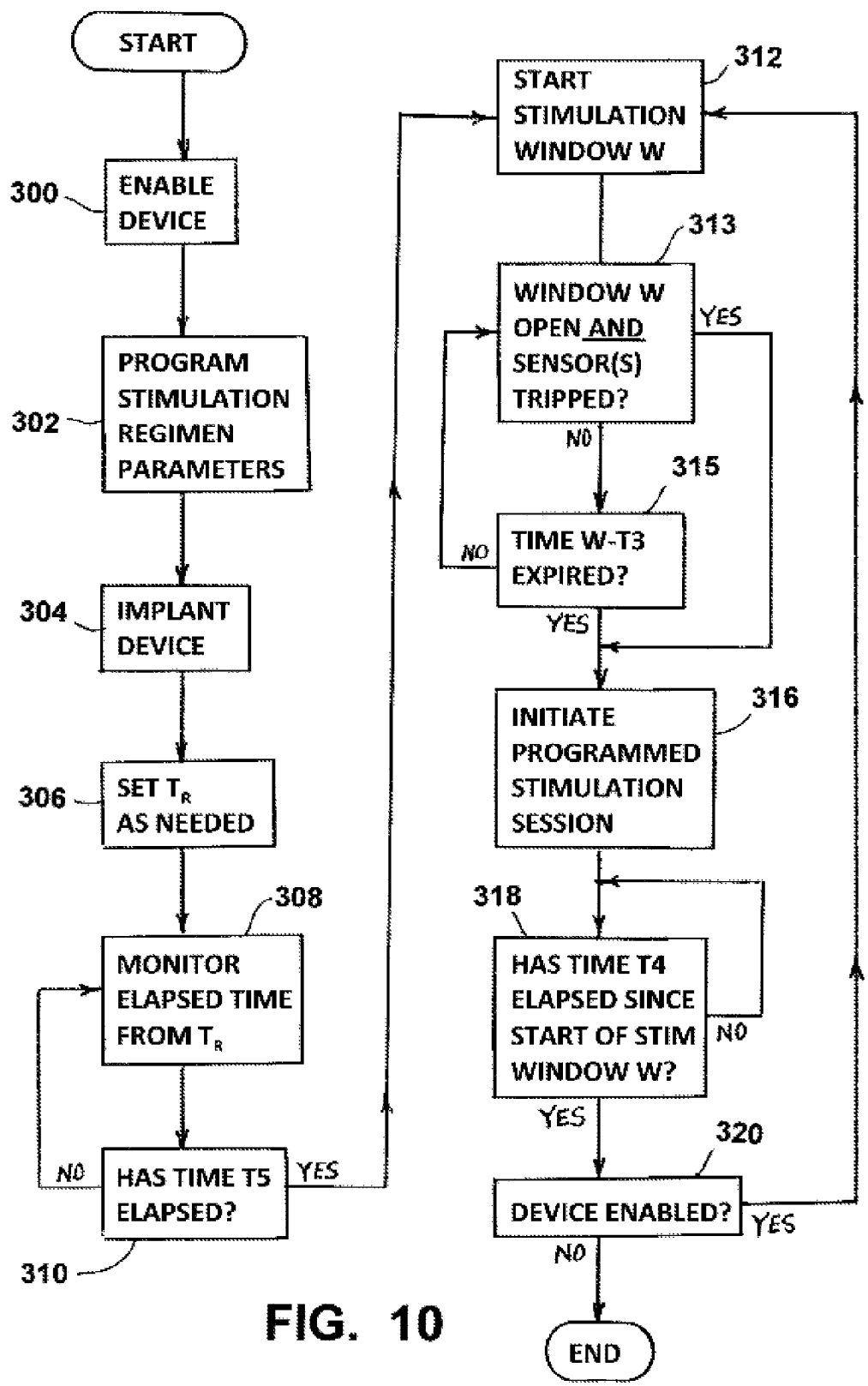
FIG. 10 is a flow diagram illustrating one representative approach for generating the sequence of stimulation windows and stimulation sessions depicted in the timing diagram of FIG. 8.

FIG. 10 is a flow diagram illustrating one representative approach for generating the sequence of stimulation windows and stimulation sessions depicted in the timing diagram of FIG. 8. As seen in FIG. 10, many of the steps associated with this flow diagram are the same as the steps shown in the flow diagram of FIG. 9, described above. That is, as seen by comparing FIG. 10 with FIG. 9, the steps shown in blocks 300, 302, 304, 306, 308 and 310 of both figures are the same. Hence, the description of these steps presented above for FIG. 9 is the same for FIG. 10.

Still referring to FIG. 10, and with a comparison to FIG. 9, it is seen that the steps of the process described in blocks 312, 316, 318 and 320 are also the same for both figures. The difference in FIG. 10 from what is shown in FIG. 9 is that the step shown in block 314 in FIG. 9 has been replaced by the steps shown in blocks 313 and 315 in FIG. 10.

Thus, as seen in FIG. 10, after the stimulation window W has been started (block 312), a determination is made as to whether the stimulation window W is still open and the sensor(s) have been tripped (block 313). The sensor(s) referred to here is the sensor(s) used to determine whether the patient is asleep. If the patient is asleep, the sensor(s) is tripped (YES branch of block 313), and the programmed stimulation session is initiated (block 316).

If the patient is not asleep, i.e., if the sensor(s) has not been tripped (NO branch of block 313), then a determination is made as to whether the time period W-T3 has expired (block 315). If the time period W-T3 has expired, then that means the sensor(s) have not tripped during the whole time (less the duration of the stimulation session T3) that the stimulation window has been open. In such event (YES branch of block 315), then the stimulation session is begun anyway (block 316) so that the patient is assured of receiving one stimulation session for each stimulation window that is open.

The preceding description has been presented only to illustrate and describe embodiments of the invention. It is not intended to be exhaustive or to limit the invention to any precise form disclosed. Many modifications and variations are possible in light of the above teaching. Thus, while the invention(s) herein disclosed has been described by means of specific embodiments and applications thereof, numerous modifications and variations could be made thereto by those skilled in the art without departing from the scope of the invention(s) set forth in the claims

What is claimed is:

1. An implantable electroacupuncture (EA) device comprising a thin, leadless, disc-shaped housing having a diameter of 2-3 cm and a thickness of 2-4 mm, electrical stimulation circuitry on the inside of the housing and two electrodes formed on the outside of the housing, with one electrode comprising a central electrode positioned in the center of one side of the housing, and with the other electrode comprising a ring electrode positioned around the edge of the disc-shaped housing, and wherein the two electrodes on the outside of the housing are coupled to the stimulation circuitry on the inside of the housing, the stimulation circuitry being configured to generate EA stimulation pulses that are applied to the electrodes following a prescribed stimulation regimen, the prescribed stimulation regimen causing EA stimulation pulses to be generated during a stimulation session of T3 minutes, which stimulation session occurs only during nighttime hours and only once every T4 days, whereby the stimulation regimen restricts the timing of when the stimulation pulses are applied to the electrodes so that, when the EA device is implanted near a desired target location of a patient, stimulation pulses are applied to the desired target location only during a stimulation session of T3 minutes that occurs during nighttime hours no more than once every T4 days.

2. The implantable EA device of claim 1 wherein the EA device is configured to be implanted near a specified acupoint of a patient, and wherein the EA stimulation pulses are applied to the electrodes, and hence to the specified acupoint, for the purpose of treating hypertension.

3. The implantable EA device of claim 2 wherein the specified acupoint is selected from a group of acupoints comprising PC5, PC6, LI4, ST36, ST37, LI11, LR3, and GB34.

4. The implantable EA device of claim 1 wherein the EA stimulation pulses are applied to the electrodes for the purpose of minimizing nondipping, including reverse dipping, of the patient's blood pressure.

5. The implantable EA device of claim 4, wherein the time period T3 comprises 15 to 120 minutes.

6. The implantable EA device of claim 5 wherein the time period T3 comprises 30 minutes.

7. The implantable EA device of claim 4, wherein the time period T4 comprises 2 to 14 days.

* * * * *